United States Patent [19]

Clemence et al.

[11] Patent Number: 4,808,609

[45] Date of Patent: * Feb. 28, 1989

[54] AMINO-(HYDROXY)ALKOXY-4-PHENYL-PROPYL INDOLES HAVING ANTIARRYTHMIC ACTIVITY

[75] Inventors: Francois Clemence; Jacques Guillaume, both of Paris; Gilles Hamon, Montrouge, all of France

[73] Assignee: Roussel Uclaf, Paris, France

[*] Notice: The portion of the term of this patent subsequent to Mar. 17, 2004 has been disclaimed.

[21] Appl. No.: 878,195

[22] Filed: Jun. 25, 1986

[30] Foreign Application Priority Data

Jun. 27, 1985 [FR] France ............... 85 09785

[51] Int. Cl.$^4$ .................. A61K 31/40; C07D 209/04
[52] U.S. Cl. .................. 514/415; 514/235.2; 514/253; 514/323; 514/418; 544/143; 544/144; 544/373; 546/201; 548/469; 548/486
[58] Field of Search .......... 548/469, 484, 486; 514/415, 418, 235.2, 253, 323; 564/347, 352; 546/201; 544/373, 143, 144

[56] References Cited

U.S. PATENT DOCUMENTS 4,387,100 6/1983 Machin .................. 548/260
4,650,811 3/1987 Guillaume ................ 514/415

FOREIGN PATENT DOCUMENTS 3343671 6/1985 Fed. Rep. of Germany .
730922 6/1955 United Kingdom .......... 564/317

Primary Examiner—Donald G. Daus
Assistant Examiner—Mark W. Noel
Attorney, Agent, or Firm—Bierman & Muserlian

[57] ABSTRACT

A compound selected from the group consisting of hydroxyalkoxy-4-phenylpropyl-indoles of the formula

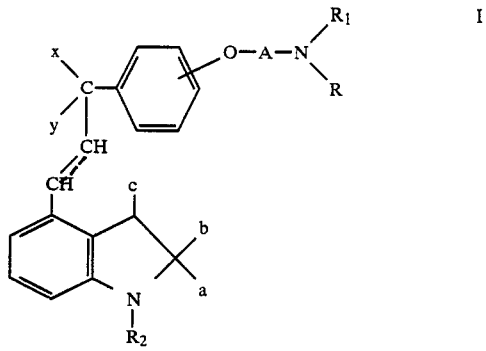

wherein R and $R_1$ are individually selected from the group consisting of hydrogen, alkyl of 1 to 5 carbon atoms, cycloalkyl of 3 to 7 carbon atoms, cycloalkylalkyl of 4 to 7 carbon atoms and aralkyl of 7 to 12 carbon atoms optionally substituted with 1 to 3 members of the group consisting of halogen, methyl, ethyl, methoxy, ethoxy, $-CF_3$, $-NO_2$, $CH_3S-$ and $-NH_2$ or $R_1$ and R together with the nitrogen atom to which they are attached form an optionally unsaturated heterocycle optionally containing $-S-$, $-O-$ or

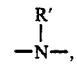

is selected from the group consisting of hydrogen, alkyl of 1 to 5 carbon atoms, phenyl, naphthyl and phenylalkyl of 7 to 12 carbon atoms, a and b form =O and c is hydrogen or a and c form a carbon-carbon bond and b is hydrogen, the dotted line is an optional double bond, A is

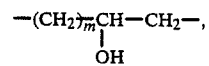

, m is 1,2 or 3, $R_2$ is selected from the group consisting of hydrogen and alkyl of 1 to 5 carbon atoms, x is selected from the group consisting of hydrogen and $-OH$ and y is hydrogen or x together with y is =O and their non-toxic, pharmaceutically acceptable acid addition salts having antiarrhythmic activity and blocking of slow calcico-sodic canals and a process and novel intermediates for their preparation.

21 Claims, No Drawings

AMINO-(HYDROXY)ALKOXY-4-PHENYLPROPYL INDOLES HAVING ANTIARRYTHMIC ACTIVITY

STATE OF THE ART

Copending U.S. patent application Ser. No. 853,030 filed Apr. 17, 1986 describes related 4-phenylpropyl-indoles having antiarrhymic activity.

OBJECTS OF THE INVENTION

It is an object of the invention to provide the novel compounds of formula I and their non-toxic, pharmaceutically acceptable acid addition salts and a novel process and novel intermediates for their preparation.

It is another object of the invention to provide novel antiarrhythmic compositions and a novel method of inducing antiarrhythmic activity in warm-blooded animals.

These and other objects and advantages of the invention will become obvious from the following detailed description.

THE INVENTION

The novel compounds of the invention are selected from the group consisting of hydroxyalkoxy-4-phenyl-propyl-indoles of the formula

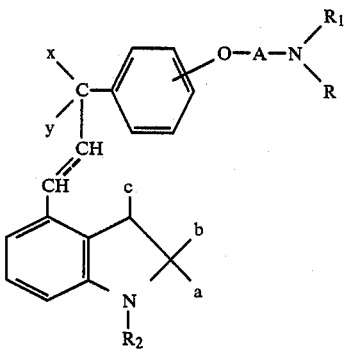

wherein R and $R_1$ are individually selected from the group consisting of hydrogen, alkyl of 1 to 5 carbon atoms, cycloalkyl of 3 to 7 carbon atoms, cycloalkylalkyl of 4 to 7 carbon atoms and aralkyl of 7 to 12 carbon atoms optionally substituted with 1 to 3 members of of the group consisting of halogen, methyl, ethyl, methoxy, ethoxy, —$CF_3$, —$NO_2$, $CH_3S$— and —$NH_2$ or $R_1$ and R together with the nitrogen atom to which they are attached form an optionally unsaturated heterocycle optionally containing —S—, —O— or $$-\underset{\underset{|}{R'}}{N}-,$$

R' is selected from the group consisting of hydrogen, alkyl of 1 to 5 carbon atoms, phenyl, naphthyl and phenylalkyl of 7 to 12 carbon atoms, a and b form =0 and c is hydrogen or a and c form a carbon-carbon bond and b is hydrogen, the dotted line is an optional double bond, A is

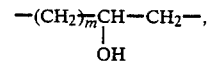

m is 1, 2 or 3, $R_2$ is selected from the group consisting of hydrogen and alkyl of 1 to 5 carbon atoms, x is selected from the group consisting of hydrogen and —OH and y is hydrogen or x together with y is =0.

Examples of alkyl of 1 to 5 carbon atoms are methyl, ethyl, propyl, isopropyl and tert.-butyl and examples of cycloalkyl of 3 to 7 carbon atoms are cyclopropyl, cyclohexyl and preferably cyclopentyl. Examples of cycloalkylalkyl of 4 to 7 carbon atoms are cyclobutyl-methyl and preferably cyclopropylmethyl and examples of optionally substituted phenylalkyl of 7 to 12 carbon atoms are benzyl and phenethyl which may have 1 to 3 substituents such as halogen, methyl, ethyl, methoxy, ethoxy, —$CF_3$, —$NO_2$, —$NH_2$ and $CH_3S$—.

Examples of heterocycles formed by

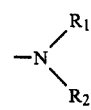

are pyrrolidino, piperidino, morpholino, piperazinyl, methylpiperazinyl, ethylpiperazinyl, propylpiperazinyl, phenylpiperazinyl and benzylpiperazinyl.

Examples of acids for the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkanesulfonic acids such as methane sulfonic acid and ethane sulfonic acid and aryl sulfonic acids such as benzene sulfonic acid and p-toluene sulfonic acid and arylcarboxylic acids such as benzoic acid.

Among the preferred compounds of formula I are those wherein a and c form a carbon-carbon bond, those wherein $R_1$ and $R_2$ are hydrogen, those wherein a and b form =0 and those wherein $R_1$ is propyl and $R_2$ is hydrogen and their non-toxic, pharmaceutically acceptable acid addition salts.

Particularly preferred compounds of formula I are 1-[2-[3-(1,1-dimethylethylamino)-2-hydroxypropoxy]-phenyl]-3-(1H-indol-4-yl)-1-propanone and 1,3-dihydro-4-[3-[2-(3-propylamino-2-hydroxypropoxy)-phenyl]-propyl]-2H-indol-2-one and their non-toxic, pharmaceutically acceptable acid addition salts.

The novel process of the invention for the preparation of a compound of formula I comprises reacting a compound of the formula

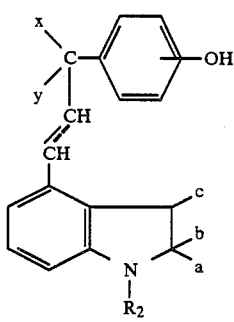　II wherein R$_2$, a, b, c, x, y and the dotted line have the above definitions with a halide of the formula

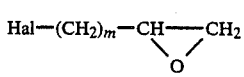　III wherein m has the above definition and Hal is chlorine, bromine or iodine to obtain a compound of the formula

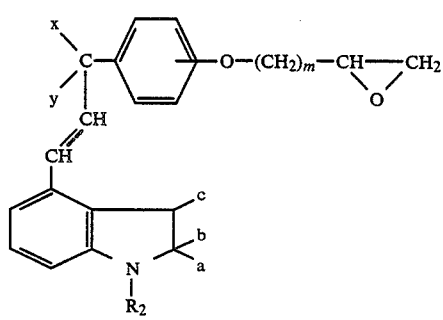　IV reacting the latter with an amine of the formula

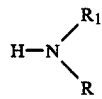　V wherein R and R$_1$ have the above definitions to obtain the corresponding compound of formula I and optionally salifying the latter to form its acid addition salt.

In a preferred mode of the process, the compounds of formulae II and III are reacted in the presence of a base such as sodium carbonate, sodium hydroxide, potassium carbonate or potassium hydroxide and Hal is preferably chlorine. The reaction of the compound of formula IV and the amine of formula V may be effected in an excess of the amine which can act as the solvent or with a solvent such as an aliphatic alcohol like ethanol.

In a variation of the process of the invention to prepare a compound of formula I, a compound of the formula

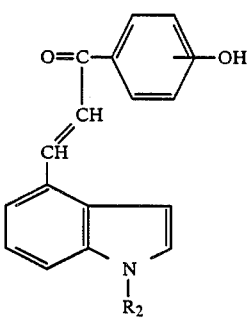　II$_A$ wherein R$_2$ has the above definition is reacted with a halide of formula III to obtain a compound of the formula

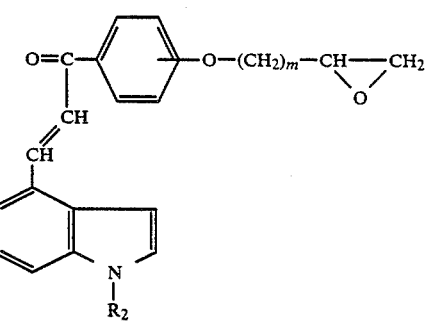　IV$_A$ which is reacted with an amine of the formula V to obtain a compound of the formula

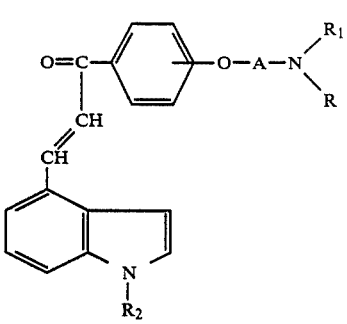　I$_A$ wherein R, R$_1$ and R$_2$ have the above definitions and either reducing the double bond of the aliphatic chain to obtain a compound of the formula

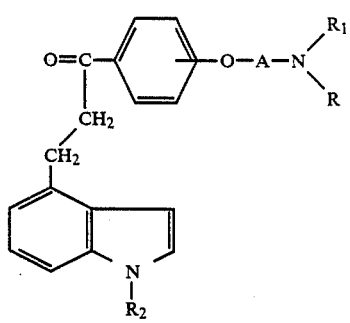　I$_B$ which may be salified or reducing the keto group of the compound of formula $I_B$ to obtain a compound of the formula

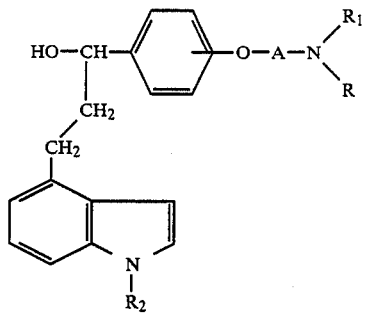 $I_C$ which may be salified or reducing the hydroxyl of formula $I_C$ to obtain a compound of the formula

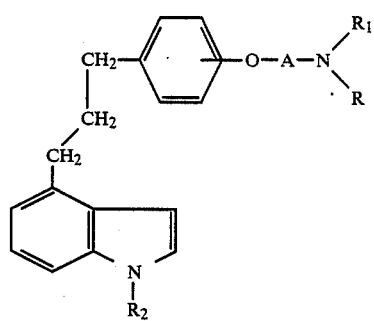 $I_D$ which may be salified or reducing the keto of a compound of formula $I_A$ to obtain a compound of the formula

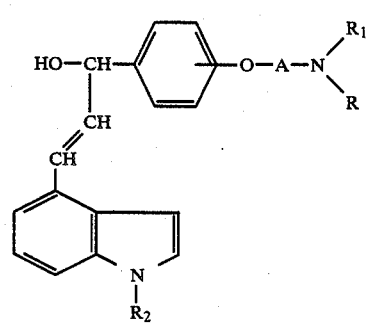 $I_E$ which may be salified or reduced at the aliphatic double bond to obtain a compound of the formula $I_D$ which may be salified or reducing the double bond and the keto group of the compound of formula $I_A$ at the same time to obtain a compound of formula $I_D$ which may be salified and a compound of formulae $I_A$, $I_B$, $I_C$, $I_D$ and $I_E$ may be reacted with a halogenation agent to obtain a compound of the formula

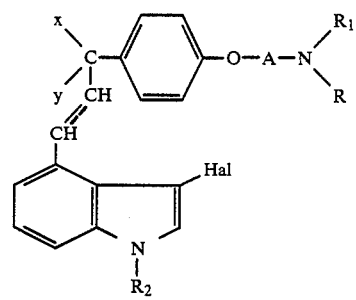 VI wherein Hal is chlorine or bromine and subjecting the latter to hydrolysis to obtain a compound of the formula

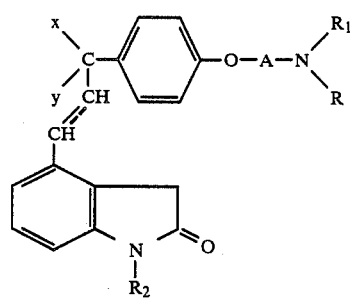 $I_F$ which may be salified.

The reduction of the aliphatic double bond of the compound of formula $I_A$ may be effected with gaseous hydrogen in the presence of a platinum or palladium catalyst in a solvent such as an alkanol of 1 to 5 carbon atoms or with gaseous hydrogen in the presence of Raney nickel in a solvent such as ethyl acetate or with sodium in ammonia in a solvent such as tetrahydrofuran with a contact time of less then 3 hours, preferably one hour.

The reduction of the keto group of the compound of formula $I_B$ may be effected with an alkali metal cyanoborohydride or borohydride such as sodium cyanoborohydride, potassium cyanoborohydride, potassium borohydride and preferably sodium borohydride.

The reduction of the hydroxy group of the compound of formula $I_C$ is preferably effected with sodium in ammonia, and preferably in a solvent such as tetrahydrofuran, with a contact time of about 6 hours.

The reduction of the keto group of the compound of formula $I_A$ may be effected with a pyridine-alkali metal borohydride complex such as pyridine-sodium borohydride in an alkanol of 1 to 5 carbon atoms such as ethanol. The reduction of the aliphatic double bond of the compound of formula $I_E$ is preferably effected with sodium in liquid ammonia as well as the simultaneous reduction of the keto group and aliphatic double bond of the compound of formula $I_A$.

The halogenation of the compounds of formulae $I_A$, $I_B$, $I_C$, $I_D$ or $I_E$ is preferably effected with the brominated pyridine complex of the formula

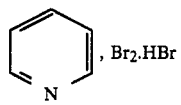, Br$_2$.HBr for bromination or with a N-halo-succinimide such as N-bromo- or N-chloro-succinimide in dioxane or preferably in acetic acid. Preferably, the halogen of the compounds of formula VI is chlorine.

When R$_1$ or R is hydrogen, the secondary amine group is protected before the halogenation reaction. Examples of known amine protective groups are trifluoroacetic acid in the presence of a base such as triethylamine in a solvent such as chloroform.

The hydrolysis of the compounds of formula VI is preferably effected with a mineral acid such as phosphoric acid, sulfuric acid and preferably hydrochloric acid in either concentrated aqueous form or preferably dilute aqueous form such as 1N. A solvent such as an aliphatic alcohol like ethanol can also be used.

The starting compounds of formula II may be prepared by reacting a compound of the formula

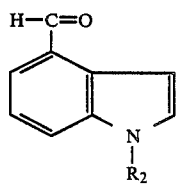 VII wherein R$_2$ has the above definition with a compound of the formula

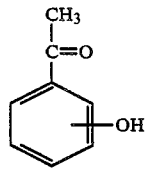 VIII to obtain a compound of the formula

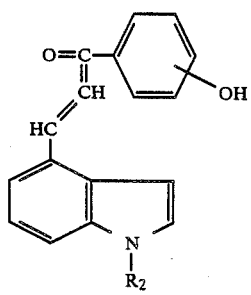 II$_A$ and either reducing the aliphatic double bond to obtain a compound of the formula

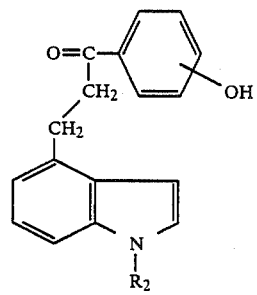 II$_B$ which may be salified or reduced at the keto group to obtain a compound of the formula

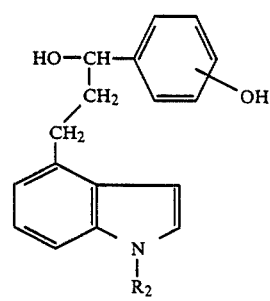 II$_C$ which may be further reduced to obtain a compound of the formula

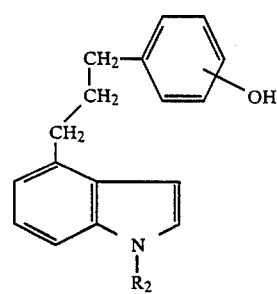 II$_D$ or reducing the keto group of the compound of formula II$_B$ to obtain a compound of formula II$_D$ or reducing the keto group of a compound of formula II$_A$ to obtain a compound of the formula

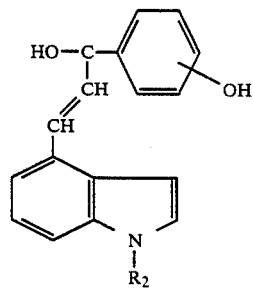 II$_E$ which may be isolated or reduced at the aliphatic double bond to obtain a compound of formula II$_D$ or simultaneously reducing the keto group and aliphatic double bond of a compound of formula II$_A$ to obtain a compound of formula II$_D$ and optionally reacting a compound of formulae II$_A$, II$_B$, II$_C$, II$_D$ or II$_E$ with a halogenation agent to obtain a compound of the formula

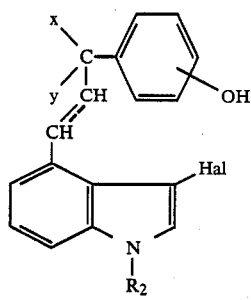

IX wherein x, y, R$_2$ and the dotted line have the above definitions and Hal is chlorine or bromine and subjecting the latter to hydrolysis to obtain a compound of the formula

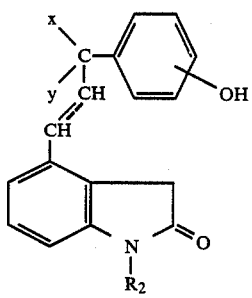

II$_F$ which may be isolated.

The reaction of the compounds of formula VII and VIII is preferably effected in the presence of a mineral base such as sodium hydroxide or potassium hydroxide in a solvent such as an alkanol of 1 to 5 carbon atoms, preferably ethanol. The reductions of the compounds of formula II may be effected under the same conditions as those for the compounds of formula I. The reduction of the compound of formula II$_B$ to form a compound of formula II$_D$ is preferably effected with hydrazine in the presence of potassium hydroxide in ethylene glycol. The halogenation and hydrolysis steps may be effected as with the corresponding compounds of formula I.

The compounds of formula VII are known and may be prepared by the process described in J. Org. Chem., Vol. 45 (1980) p. 3350, for example.

The compounds of formula I have a basic character and the acid addition salts thereof may be prepared by reacting essentially stoichiometric amounts of the acid and the compound of formula I with or without isolation of the base.

The novel antiarrhythmic compositions of the invention are comprised of an antiarrhythmically effective amount of at least one compound of formula I and their non-toxic, pharmaceutically acceptable acid addition salts and an inert pharmaceutical carrier or excipient. The compositions may be in the form of tablets, dragees, capsules, granules, suppositories and injectable solutions or suspensions.

Examples of suitable excipients are talc, arabic gum, lactose, starch, magnesium stearate, cocoa butter, aqueous and non-aqueous vehicles, animal or vegetable fatty substances, paraffinic derivatives, glycols, various wetting agents, emulsifiers and dispersants and preservatives.

The compositions have remarkable antiarrhythmic activity and are capable of blocking the slow calcicosodic canals and are useful for the treatment of cardiac insufficiency, all forms of angor and for the treatment of arrhythmias.

The preferred compositions of the invention are those wherein a and c form a carbon-carbon bond and especially those wherein R$_1$ and R$_2$ are hydrogen as well as those wherein a and b form =O and especially when R$_1$ is propyl and R$_2$ is hydrogen and their non-toxic, pharmaceutically acceptable acid addition salts.

The novel method of the invention for the treatment of arrhythmia in warm-blooded animals, including humans, comprises administering to warm-blooded animals an antiarrhythmically effective amount of at least one compound of formula I and its non-toxic, pharmaceutically acceptable acid addition salts. The compounds may be administered orally, rectally or parenterally and the usual daily dose is 0.7 to 15 mg/kg depending on the condition treated, the specific compound and the method of administration. For example, the compound of Example 1 may be orally administered at a daily dose of 1.5 to 6 mg/kg for the treatment of ventricular, supraventricular and junctional arrhythmias.

The novel intermediates of the invention are the compounds of formulae IV and VI.

In the following examples there are described several preferred embodiments to illustrate the invention. However, it should be understood that the invention is not intended to be limited to the specific embodiments.

EXAMPLE 1

(E) butenedioate (1,2) of 1-[2-[3-(1,1-dimethylethylamino)-2-hydroxypropoxy]-phenyl]-3-(1H-indol-4-yl)-1-propanone

STEP A 1-(2-hydroxyphenyl)-3-(1H-indol-4-yl)-2-propen-1-one 0.5 ml of 38% potassium hydroxide solution was added with stirring under an inert atmosphere at 30° C. to a mixture of 0.132 g of indole-4-carboxaldehyde, 0.1 ml of 2-hydroxy-acetophenone and 0.189 g of triethylbenzylammonium in 2 ml of ethanol and after stirring at 30° C. for 23 hours, the mixture was diluted with water and extracted with ethyl acetate. The organic phase was washed with water, dried and evaporated to dryness under reduced pressure. The residue was chromatographed over silica and eluted with methylene chloride to obtain 159 mg of 1-(2-hydroxyphenyl)-3-(1H-indol-4-yl)-2-propen-1-one melting 164° C.

STEP B 1-(2-hydroxyphenyl)-3-(1H-indol-4-yl)-1-propanone

A mixture of 200 mg of the product of Step A in 10 ml of methanol was hydrogenated in the presence of palladized activated charcoal at room temperature until absorption ceased and was then filtered. The filtrate was evaporated to dryness and the residue was chromatographed over silica. Elution with a 6-3-1 cyclohexane-dichloromethane-triethylamine mixture yielded 143 mg of 1-(2-hydroxyphenyl)-3-(1H-indol-4-yl)-1-propanone melting at ≃143° C.

UV Spectrum (ethanol):

| | | |
|---|---|---|
| Max. at 214 nm | $E_1^1 = 2,080$ | $\epsilon = 55,200$ |
| Max. at 254 nm | $E_1^1 = 555$ | $\epsilon = 14,700$ |
| Inflex. at 275 nm | $E_1^1 = 295$ | |
| Inflex. at 286 nn | $E_1^1 = 220$ | |
| Max. at 323 nm | $E_1^1 = 117$ | $\epsilon = 4,700$ |

STEP C

1-[2-[(2-oxiranyl)-methoxy]-phenyl]-3-(1H-indol-4-yl)-1-propanone 9.54 g of potassium carbonate and then 16.2 ml of epichlorohydrin were added to a solution of 4.58 g of the product of Step B in 80 ml of acetone and the mixture was refluxed for 43 hours under an inert atmosphere. The mixture was filtered and the filtrate was evaporated to dryness. The residue was chromatographed over silica and was eluted with a 95-5 dichloroethane-ethyl acetate mixture to obtain 5.00 g of 1-[2-[(2-oxiranyl)-methoxy]-phenyl]-3-(1H-indol-4-yl)-1-propanone melting at 72° C.

UV Spectrum (ethanol):

| | | |
|---|---|---|
| Max. at 214 nm | $E_1^1 = 1,625$ | $\epsilon = 52,200$ |
| Max. at 248 nm | $E_1^1 = 307$ | $\epsilon = 9,900$ |
| Max. at 270 nm | $E_1^1 = 269$ | $\epsilon = 8,650$ |
| Max. at 278 nm | $E_1^1 = 268$ | |
| Max. at 288 nm | $E_1^1 = 232$ | $\epsilon = 7,450$ |
| Inflex. at 300 nm | $E_1^1 = 118$ | $\epsilon = 3,800$ |

STEP D (E) butenedioate of (1,2) 1-[2-[3-(1,1-dimethylethylamino)-2-hydroxypropoxy]-phenyl]-3-(1H-indol-4-yl)-1-propanone A mixture of 1.25 g of the product of Step C, 4.1 ml of tert.-butylamine and 15 ml of methanol was refluxed for 2½ hours and was then evaporated to dryness. The residue was chromatographed over silica and eluted with an 8-1-1 chloroform-methanol-triethylamine mixture to obtain 1.52 g of product. A solution of 3.36 g of the said product in 55 ml of ethanol was admixed with a hot solution of 0.49 g of fumaric acid in 25 ml of ethanol at 80° C. and the mixture was filtered. The product was dried under reduced pressure to obtain 2.46 g of (E) butenedioate (1,2) 1-[2-[3-(1,1-dimethylethylamino)-2-hydroxypropoxy]-phenyl]-3-(1H-indol-4-yl)-1-propanone melting at 209° C. after crystallization from methanol.

Analysis: $C_{24}H_{30}N_2O_3 \cdot 0.5 C_4H_4O_4$; molecular weight=452.555. Calculated: %C 69.0; %H 7.13; %N 6.14. Found: 68.8; 7.2; 6.3.

EXAMPLE 2

(E) butenedioate (1,2) 1-[2-[2-hydroxy-3-propylamino-propoxy]-phenyl]-3-(1H-indol-4-yl)-1-propanone A solution of 2.85 g of the product of Step C of Example 1, 5.12 ml of propylamine and 30 ml of methanol was refluxed for 45 minutes and was then evaporated to dryness. The residue was chromatographed over silica and was eluted with a 9-1 ethyl acetate-triethylamine mixture to obtain 3.4 g of product which was dissolved in 50 ml of ethanol and 1.04 g of fumaric acid was added. The mixture was filtered and the product was dried under reduced pressure to obtain 1.77 g of (E) butenedioate (1,2) 1-[2-[2-hydroxy-3-propylamino-propoxy]-phenyl]-3-(1H-indol-4-yl)-1-propanone melting at 183° C. after crystallization from a methanol-ethanol mixture.

Analysis: $(C_{23}H_{28}N_2O_3)_2 \cdot C_4H_4O_4$; molecular weight=997.127. Calculated: %C 68.47; %H 6.89; %N 6.39. Found: 68.3; 7.1; 6.5.

EXAMPLE 3

1-[2-[3-(1,1-dimethylethylamino]-2-hydroxypropoxy]-phenyl]-3-(1H-indol-4-yl]-2-propen-1-one

STEP A

1-[2-[(2-oxiranyl)-methoxy]-phenyl]-3-(1H-indol-4-yl)-2-propen-1-one

First 3.46 g of potassium carbonate and then 10.5 ml of epichlorohydrin were added to a solution of 4 g of 1-[2-hydroxyphenyl]-3-(1H-indol-4-yl)-2-propen-1-one in 80 ml of acetone and the mixture was refluxed for 50 hours under an inert atmosphere and was filtered. The filtrate was evaporated to dryness and the residue was chromatographed over silica. Elution with a 95-5 dichloromethane-ethyl acetate mixture yielded 2.26 g of 1-[2-[(2-oxiranyl)-methoxy]-phenyl]-3-(1H-indol-4-yl)-2-propen-1-one.

UV Spectrum (ethanol):

| | | |
|---|---|---|
| Max. at 213 nm | $E_1^1 = 947$ | $\epsilon = 30,200$ |
| Max. at 266 nm | $E_1^1 = 407$ | $\epsilon = 13,000$ |
| Inflex. at 340 nm | $E_1^1 = 262$ | |
| Max. at 390 nm | $E_1^1 = 442$ | $\epsilon = 14,100$ |

STEP B

1-[2-[3-(1,1-dimethylethylamino)-2-hydroxypropoxy]-phenyl]-3-(1H-indol-4-yl)-2-propen-1-one A solution of 2.13 g of the product of Step A, 7.1 ml of tert.-butylamine and 22 ml of methanol was refluxed for 2½ hours and was then evaporated to dryness. The residue was chromatographed over silica and eluted with an 8-1-1 chloroform-methanol-triethylamine mixture to obtain 2.6 g of 1-[2-[3-(1,1-dimethylethylamino)-2-hydroxypropoxy]-phenyl]-3-(1H-indol-4-yl)-2-propen-1-one.

UV Spectrum (ethanol):

| | | |
|---|---|---|
| Max. at 215 nm | $E_1^1 = 433$ | $\epsilon = 17.000$ |
| Max. at 264 nm | $E_1^1 = 171$ | $\epsilon = 6,700$ |
| Inflex at 347 nm | $E_1^1 = 114$ | |
| Max. at 388 nm | $E_1^1 = 174$ | $\epsilon = 6,800$ |

EXAMPLE 4

1-[2-[3-(1,1-dimethylethylamino)-2-hydroxypropoxy]-phenyl]-3-(1H-indol-4-yl)-1-propanone A mixture of 2.6 g of the product of Example 3 in 50 ml of methanol was hydrogenated in the presence of palladized active charcoal until absoprtion ceased and was filtered. The filtrate was evaporate to dryness and the residue was chromatographed over silica. Elution with a 6-3-1 chloroform-acetone-triethylamine mixture yielded 1.97 g of 1-[2-[3-(1,1-dimethylethylamino)-2-hydroxypropoxy]phenyl]-3-(1H-indol-4-yl)-1-propanone.

UV Spectrum (ethanol):

| | | |
|---|---|---|
| Max. at 214 nm | $E_1^1 = 1,244$ | $\epsilon = 49,100$ |
| Max. at 247 nm | $E_1^1 = 220$ | $\epsilon = 8,700$ |

| | | |
|---|---|---|
| Max. at 269 nm | $E_1^1 = 196$ | $\epsilon = 7,700$ |
| Max. at 275 nm | $E_1^1 = 194$ | $\epsilon = 7,650$ |
| Inflex. at 286 nm | $E_1^1 = 164$ | |
| Inflex. at 300 nm | $E_1^1 = 85$ | $\epsilon = 3,350$ |

EXAMPLE 5

1,3-dihydro-4-[3-[2-[3-(1,1-dimethylethylamino)-2-hydroxypropoxy]-phenyl]-3-oxo-propyl]-2H-indol-2-one and its neutral fumarate

STEP A:

3-(3-chloro-1H-indol-4-yl)-1-[2-[3-(1,1-dimethylethylamino)-2-hydroxypropoxy]-phenyl]-1-propanone A mixture of 8.6 g of 1-[2-[3-(1,1-dimethylethylamino)-2-hydroxypropoxy]-phenyl]-3-(1H-indol-4-yl)-1-propanone, 3 g of N-chlorosuccinimide and 170 ml of acetic acid was stirred at room temperature for 2 hours and was then diluted with water. The mixture was made alkaline by addition of sodium hydroxide and was extracted with ethyl acetate. The organic phase was washed with water, dried and evaporated to dryness under reduced pressure. The residue was chromatographed over silica and eluted with a 6-3-1 chloroform-acetone-triethylamine mixture to obtain 6.37 g of 3-(3-chloro-1H-indol-4-yl)-1-[2-[3-(1,1-dimethylethylamino)-2-hydroxypropoxy]-phenyl]-1-propanone.

STEP B 1,3-dihydro-4-[3-[2-[3-(1,1-dimethylethylamino)-2-hydroxypropoxy]-phenyl]-3-oxopropyl]-2H-indol-2-one and its neutral fumarate A mixture of 6.37 g of the product of Step A, 192 ml of N hydrochloric acid and 192 ml of ethanol was stirred for 17 hours at room temperature and was then diluted with water. The mixture was made alkaline by addition of sodium hydroxide and was extracted with ethyl acetate. The organic phase was washed with water, dried and evaporated to dryness under reduced pressure. The residue was chromatographed over silica and eluted with a 6-3-1 chloroform-acetone-triethylamine mixture to obtain 2.32 g of 1,3-dihydro-4-[3-[2-[3-(1,1-dimethylethylamino)-2-hydroxypropoxy]-phenyl]-3-oxopropyl]-2H-indol-2-one.

Preparation of the neutral fumarate 2.12 g of the said product were dissolved in 80 ml of isopropanol and 599 mg of fumaric acid were added thereto. The mixture was filtered and the crystals were dried at 120° C. to obtain 1.77 g of crude product which was crystallized from a 2-1 ethanol-methanol mixture to obtain 1.21 g of the neutral fumarate of the said base melting at 238° C.

Analysis: $(C_{24}H_{30}N_2O_4).0.5C_4H_4O_4$; molecular weight=468.554. Calculated: %C 66.65; %H 6.88; %N 5.98. Found: 66.3; 6.9; 5.8.

EXAMPLE 6

1,3-dihydro-4-[3-oxo-3-[2-(2-hydroxy-3-propylaminopropoxy)-phenyl]-propyl]-2H-indol-2-one and its acid oxalate

STEP A 3-(3-chloro-1H-indol-4-yl)-1-[2-[2-hydroxy-3-propylamino-propoxy]-phenyl]-1-propanone Using the procedure of Step A of Example 5, 6.3 g of the free base of Example 2, 120 ml of acetic acid and 2.43 g of N-chlorosuccinimide were reacted to obtain 5.6 g of 3-(3-chloro-1H-indol-4-yl)-1-[2-[2-hydroxy-3-propylamino-propoxy]-phenyl]-1-propanone.

STEP B 1,3-dihydro-4-[3-oxo-3-[2-[2-hydroxy-3-propylaminopropoxy]-phenyl]-propyl]-2H-indol-2-one and its acid oxalate Using the procedure of Step B of Example 5, 5.6 g of the product of Step A were reacted to obtain 2.42 g of 1,3-dihydro-4-[3-oxo-3-[2-[2-hydroxy-3-propylaminopropoxy]-phenyl]-propyl]-2H-indol-2-one. 768 g of oxalic acid were added to a hot solution of 2.42 g of the said compound and 20 ml of ethanol and the mixture was cooled and filtered. The crystals were dried under reduced pressure at 80° C. to obtain 1.2 g of crude product which were crystallized from ethanol to obtain 0.9 g of the acid oxalate of the base melting at 120° C.

Analysis: $(C_{23}H_{28}N_2O_4).C_2H_2O_4$; molecular weight=486.526. Calculated: %C 61.72; %H 6.21; %N 5.76. Found: 62.0; 6.1; 5.8.

EXAMPLE 7

1-(1,1-dimethylethylamino)-3-[2-[3-(1H-indol-4-yl)-propyl]-phenoxy]-2-propanol and its neutral fumarate

STEP A 2-[3-(1H-indol-4-yl)-propyl]-phenol 22.6 ml of hydrazine hydrate and then 11.6 g of 1-(2-hydroxyphenyl)-3-(1H-indol-4-yl)-1-propanone were slowly added with stirring to 50 ml of diethyleneglycol and then 20 ml of 78% potassium hydroxide were added thereto. The mixture was heated at 140° C. under an inert atmosphere for 30 minutes and the water and excess hydrazine hydrate were distilled at 210° C. with stirring over two hours and the mixture was cooled and diluted with water. The mixture was extracted with ethyl acetate and the organic phase was washed with water, dried, filtered and evaporated to dryness. The residue was chromatographed over silica and eluted with methylene chloride to obtain 8.613 g of 2-[3-(1H-indol-4-yl)-propyl]-phenol melting at ≅89° C.

UV Spectrum (ethanol):

| | | |
|---|---|---|
| Max. at 219 nm | $E_1^1 = 1,705$ | $\epsilon = 42,900$ |
| Inflex. at 260 nm | $E_1^1 = 313$ | |
| Max. at 273 nm | $E_1^1 = 380$ | $\epsilon = 9,550$ |
| Inflex. at 278 nm | $E_1^1 = 375$ | |
| Max. at 289 nm | $E_1^1 = 225$ | $\epsilon = 5,650$ |

Inflex. at 310 nm
Inflex. at 334 nm

STEP B

4-[3-[2-[(2-oxiranyl)-methoxy]-phenyl]-propyl]-1H-indole 0.235 g of potassium carbonate and then 0.6 ml of epichlorohydrin were added under an inert atmosphere at room temperature to a solution of 0.284 g of the product of Step A in 4 ml of acetone and the mixture was refluxed for 8 hours. Another 1.8 ml of epichlorohydrin were added with stirring and the mixture was refluxed for 21 hours and was then filtered. The filtrate was evaporated to dryness under reduced pressure and the residue was chromatographed over silica. Elution with methylene chloride yielded 0.283 g of 4-[3-[2-[(2-oxiranyl)-methoxy]-phenyl]-propyl]-1H-indole.

STEP C
1-(1,1-dimethylethylamino)-3-[2-[3-[1H-indol-4-yl]-propyl]-phenoxy]-2-propanol and its neutral fumarate A mixture of 2.2 g of the product of Step B and 7.6 ml of tert.-butylamine and 20 ml of methanol was heated at 80° C. for 2 hours and was evaporated to dryness. The residue was chromatographed over silica and eluted with a 6-3-1 chloroform-acetone-triethylamine mixture to obtain 2.7 g of 1-(1,1-dimethylethylamino)-3-[2-[3-[1H-indol-4-yl]-propyl]-phenoxy]-2-propanol melting at 96° C.

A solution of 1.84 g of the said product in 50 ml of ethanol was admixed with 0.557 g of fumaric acid at room temperature under an inert atmosphere and the mixture was filtered. The crystals were dried under reduced pressure to obtain 1.67 g of product which was crystallized from ethanol to obtain 1.31 g of the neutral fumarate of the above compound melting at 200° C.

Analysis: $(C_{24}H_{32}N_2O_2).0.5C_4H_4O_4$; molecular weight=438.57. Calculated: %C 71.21; %H 7.81; %N 6.39. Found: 71.5; 8.1; 6.3.

EXAMPLE 8

1-[2-[3-(1H-indol-4-yl)-propyl]-phenoxy]-3-propylamino-2-propanol and its neutral fumarate Using the procedure of Step C of Example 7, 2.75 g of the product of Step B of Example 7 and 7.6 ml of propylamine were reacted and the product was chromatographed over silica. Elution with a 9-1 ethyl acetate-triethylamine mixture yielded 2.62 g of 1-[2-[3-(1H-indol-4-yl)-propyl]-phenoxy]-3-propylamino-2-propanol melting at 99°–100° C.

1.8 g of the said product andd 0.569 g of fumaric acid were reacted in isopropanol to obtain 1.26 g of the neutral fumarate of the said product melting at 163° C.

Analysis: $(C_{23}H_{30}N_2O_2).0.5C_4H_4O_4$; molecular weight=424.55. Calculated: %C 70.73; %H 7.60; %N 6.60. Found: 70.5; 7.7; 6.5.

EXAMPLE 9

1,3-dihydro-4-[3-[2-[2-hydroxy-3-propylamino-propoxy]-phenyl]-propyl]-2H-indol-2-one

STEP A
N-[3-[2-[3-(1H-indol-4-yl)-propyl]-phenoxy]-2-hydroxy-propyl]-N-propyl-trifluoroacetamide 9.68 ml of trifluoroacetic acid anhydride were added at less than 10° C. under an inert atmosphere to a mixture of 4.93 g of the base of Example 8, 51 ml of chloroform and 19.3 ml of triethylamine and the mixture was stirred for one hour and was diluted with water. The mixture was extracted with ethyl acetate and the organic phase was washed with water, dried and evaporated to dryness under reduced pressure. The residue was chromatographed over silica and eluted with a 6-3-1 chloroform-acetone-triethylamine mixture to obtain 6.3 g of N-[3-[2-[3-(1H-indol-4-yl)-propyl]-phenoxy]-2-hydroxy-propyl]-N-propyl-trifluoroacetamide.

STEP B
N-[3-[2-[3-(3-chloro-1H-indol-4-yl)-propyl]-phenoxy]-2-hydroxypropyl]-N-propyl-trifluoroacetamide A mixture of 6.3 g of the product of Step A, 100 ml of dioxane and 2 g of N-chlorosuccinimide was stirred under an inert atmosphere for 19 hours at room temperature and was then diluted with water. The mixture was extracted with ethyl acetate and the organic phase was washed with water, dried and evaporated to dryness. The residue was chromatographed over silica and eluted with a 6-3-1 chloroform-cyclohexane-triethylamine mixture to obtain 4.73 g of N-[3-[2-[3-(3-chloro-1H-indol-4-yl)-propyl]-phenoxy]-2-hydroxypropyl]-N-propyl-trifluoroacetamide.

STEP C
1,3-dihydro-4-[3-[2-[2-hydroxy-3-propylamino-propoxy]-phenyl]-propyl]-2H-indol-2-one A mixture of 4.66 g of the product of Step B and 260 ml of N hydrochloric acid was refluxed under an inert atmosphere for 3 hours and was diluted with water. The mixture was made alkaline by sodium hydroxide addition and was extracted with ethyl acetate. The organic was washed with water, dried and evaporated to dryness. The residue was triturated with ether and dried at 100° C. under reduced pressure to obtain 2.19 g of 1,3-dihydro-4-[3-[2-[2-hydroxy-3-propylamino-propoxy]-phenyl]-propyl]-2H-indol-2-one which melted at 122° C. after crystallization from isopropanol.

Analysis: $C_{23}H_{30}N_2O_3$; molecular weight=382.506. Calculated: %C 72.22; %H 7.90; %N 7.12. Found: 72.1; 7.9; 7.3.

EXAMPLE 10

Tablets were prepared containing 100 ml of the neutral fumarate of 1-[2-[3-(1,1-dimethylethylamino)-2-hydroxypropoxy]-phenyl]-3-(1H-indol-4-yl)-1-propanone or the neutral fumarate of 3-(1H-indol-4-yl)-1-[2-[2-hydroxy-3-propylamino-propoxy]-phenyl]-1-propanone and sufficient excipient of lactose, starch, talc and magnesium stearate for a final tablet weight of 150 mg.

PHARMACOLOGICAL STUDY

A. Anti-arrhythmic activity in the rat

Male rats weighing 300–350 g anesthetized intraperitoneally with 1.20 g/kg of urethane were tracheotomized and subjected to artificial respiration (40–50 breaths of 3 ml/minute). Needles were implanted subcutaneously to record the eletrocardiogram of the rats on the derivation signal DII. The products under test were administered intravenously or orally. Five minutes after the administration of the product intravenously or 1 hour after administration orally, the jugular vein of the rats was perfused with 10 µg/min. of an acqnitine solution and the time was noted of the appearance of disturbances of the cardiac rhythm (10 µg of aconitine corresponding to the perfusion of a volume of 0.2 ml of solution. The results were expressed as a percentage of the extension of the time of appearance of the cardiac rhythm disturbances as compared to controls and as a function of the dose of the product under test.

The results of the following Table show that the products of the present invention are endowed with remarkable anti-arrhythmic properties.

| Product of Example | Route of Administration | Dose in mg/kg | % extension of time |
|---|---|---|---|
| 1 | oral | 25 | 142 |
|   |   | 10 | 39 |
|   |   | 5 | 41 |
|   | IV | 0.5 | 28 |
| 2 | IV | 1 | 32 |
| 5 | oral | 10 | 47 |
|   | IV | 0.5 | 66 |
| 6 | IV | 0.25 | 31 |
| 7 | IV | 2.5 | 41 |

-continued

| Product of Example | Route of Administration | Dose in mg/kg | % extension of time |
|---|---|---|---|
| 8 | IV | 2.5 | 25.5 |
| 9 | IV | 0.5 | 45 |

B. Anti-calcic activity in vitro

Caudal arteries of rats were cut into spirals and attached to tension indicators and were kept in tanks of 25 ml of Krebs buffer-sodium bicarbonate (NaCl: 120.8 mM, KCl: 5.9 mM, $MgCl_2$: 1.2 mM, $NaH_2PO_4$: 1.2 mM, $NaHCO_3$: 15.5 mM, glucose: 12.6 mM) at 37° C. gassed with a mixture of $O_2$: 95%—$CO_2$—5%. The preparations were depolarized by a buffer solution with a concentration of 100 mM of $K^+$ ions (NaCl: 26.7 mM, KCl: 100 mM, $MgCl_2$ 1.2 mM, $NaH_2PO_4$: 1.3 mM, $NaHCO_3$: 15.5 mM, glucose: 12.6 mM).

250 µl of solutions of calcium chloride were added so that an increasing range of concentrations of $Ca^{2+}$ ions going from 0.1 to 3.0 mM was obtained. The contractions of the arteries were recorded and in this way a control range was established. The operation was repeated with the range of $Ca^{2+}$ ions every 15 minutes, and the preparation was washed four times after each range. When a stable response was obtained, the operation was carried out with the ranges of $Ca^{2+}$ ions in the presence of different concentrations of the product under test until a stable response was obtained.

The contractions of the arteries depend on the entry of the $Ca^{2+}$ ions into the cells of the smooth muscles and they are caused by the depolarization of the smooth muscle by the $K^+$ ions by the action of the noradrenaline liberated at the presynaptic level. By repeating the operation with the arteries denervated by the action of 6-OH dopamine, the action due to the noradrenaline alone is suppressed.

The results are expressed in IC 50 (inhibiting concentration 50) which is the concentration of the product under test which inhibits by 50% the contraction due to the $K^+$ ions. From the results appearing in the following Table, it was established that the products of the invention possess a strong anti-calcic activity.

| Product of Example | IC 50 in µM |
|---|---|
| 1 | 0.4 |
| 2 | 3.8 |
| 6 | 3.6 |
| 7 | 0.64 |
| 8 | 1.4 |

B. Study of the acute toxicity

The lethal doses $LD_0$ were evaluated for the different compounds tested after oral administration to mice. The maximum dose which does not cause any mortality in 8 days is called the $LD_0$ and the following results were obtained:

| Product of Example | $LD_0$ in mg/kg |
|---|---|
| 1 | 100 |
| 2 | 100 |
| 5 | >400 |
| 6 | 100 |
| 7 | >400 |
| 8 | >400 |

Various modifications of the products and method of the invention may be made without departing from the spirit or scope thereof and it is to be understood that the invention is intended to be limited only as defined in the appended claims.

What we claim is:

1. A compound selected from the group consisting of hydroxyalkoxy-4-phenylpropyl-indoles of the formula

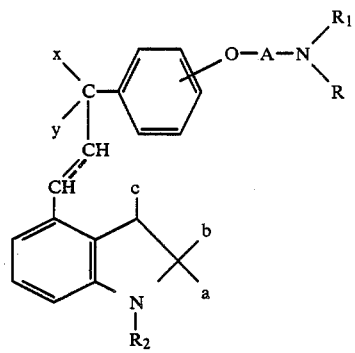

wherein R and $R_1$ are individually selected from the group consisting of hydrogen, alkyl of 1 to 5 carbon atoms, cycloalkyl of 3 to 7 carbon atoms, cycloalkylalkyl of 4 to 7 carbon atoms and aralkyl of 7 to 12 carbon atoms optionally substituted with 1 to 3 members of the group consisting of halogen, methyl, ethyl, methoxy, ethoxy, —$CF_3$, —$NO_2$, $CH_3S$— and —$NH_2$ or $R_1$ and R together with the nitrogen atom to which they are attached form a heterocycle selected from the group consisting of pyrrolidino, piperidino, morpholino, piperazinyl, methylpiperazinyl, ethylpiperazinyl, propylpiperazinyl, phenylpiperazinyl and benzylpiperazinyl, a and b form =0 and c is hydrogen or a and c form a carbon-carbon bond and b is hydrogen, the dotted line is an optional double bond, A is

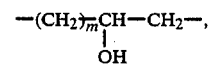

m is 1, 2 or 3, $R_2$ is selected from the group consisting of hydrogen and alkyl of 1 to 5 carbon atoms, x is selected from the group consisting of hydrogen and —OH and y is hydrogen or x together with y is =0 and their non-toxic, pharmaceutically acceptable acid addition salts.

2. A compound of claim 1 wherein a and c are a carbon-carbon bond.

3. A compound of claim 2 wherein $R_1$ and $R_2$ are hydrogen.

4. A compound of claim 1 wherein a and b are =0.

5. A compound of claim 4 wherein $R_1$ is propyl and $R_2$ is hydrogen.

6. A compound of claim 1 selected from the group consisting of 1-[2-[3-(1,1-dimethylethylamino)-2-hydroxypropoxy]-phenyl]-3-(1H-indol-4-yl)-1-propanone and its non-toxic, pharameutically acceptable acid addition salts.

7. A compound of claim 1 selected from the group consisting of 1,3-dihydro-4-[3-(2-[3-propylamino-2-hydroxypropoxy]-phenyl]-propyl]-2H-indol-2-one and its non-toxic, pharmaceutically acceptable acid addition salts.

8. An antiarrhythmic composition comprising an antiarrhythmically effective amount of at least one compound of claim 1 and an inert pharmaceutical carrier.

9. A composition of claim 8 wherein in the compound a and c form a carbon-carbon bond.

10. A composition of claim 9 wherein in the compound $R_1$ and $R_2$ are hydrogen.

11. A composition of claim 8 wherein in the compound a and b form =0.

12. A composition of claim 11 wherein in the compound $R_1$ is propyl and $R_2$ is hydrogen.

13. A composition of claim 8 wherein the active compound is selected from the group consisting of 1-[2-[3-(1,1-dimethylethylamino)-2-hydroxypropoxy]-phenyl]-3-(1H-indol-4-yl)-1-propanone and its non-toxic, pharmaceutically acceptable acid addition salts.

14. A composition of claim 8 wherein the active compound is selected from the group consisting of 1,3-dihydro-4-[3-(2-[3-propylamino-2-hydroxypropoxy]-phenyl)-propyl]-2H-indol-2-one and its non-toxic, pharmaceutically acceptable acid addition salts.

15. A method of inducing antiarrhythmic activity in warm-blooded animals comprising administering to warm-blooded animals an antiarrhythmically effective amount of at least one compound of claim 1.

16. A method of claim 15 wherein in the compound a and c form a carbon-carbon bond.

17. A method of claim 16 wherein in the compound $R_1$ and $R_2$ are hydrogen.

18. A method of claim 15 wherein in the compound a and b for =0.

19. A method of claim 18 wherein in the compound $R_1$ is propyl and $R_2$ is hydrogen.

20. A method of claim 15 wherein the active compound is selected from the group consisting of 1-[2-[3-(1,1-dimethylethylamino)-2-hydroxypropoxy]-phenyl]-3-(1H-indol-4-yl)-1-propanone and its non-toxic, pharmaceutically acceptable acid addition salts.

21. A method of claim 15 wherein the active compound is selected from the group consisting of 1,3-dihydro-4-[3-(2-[3-propylamino-2-hydroxypropoxy]-phenyl]-propyl]-2H-indol-2-one and its non-toxic, pharmaceutically acceptable acid addition salts.

* * * * *